United States Patent [19]
Moore

[11] 4,333,128
[45] Jun. 1, 1982

[54] MIRROR FOR THE APHAKIC EYE

[76] Inventor: Francis D. Moore, 66 Heath St., Brookline, Mass. 02146

[21] Appl. No.: 176,672

[22] Filed: Aug. 11, 1980

[51] Int. Cl.³ .............................................. E21V 33/00
[52] U.S. Cl. ................................... 362/135; 362/138; 362/140; 362/296; 362/347
[58] Field of Search .............. 362/135, 138, 140, 296, 362/347

[56] References Cited
U.S. PATENT DOCUMENTS
3,908,119 9/1975 Zeytoanian ..................... 362/140

*Primary Examiner*—Stephen J. Lechert, Jr.

[57] ABSTRACT

Apparatus comprising a spheroidal concave reflector is described for imparting vision to the aphakic eye without the use of a transparent external lens or aperture. A critical radius for the reflector between about 4½″ and 9½″ is defined, and associated apparatus for the convenient illumination and inspection of the eye is described.

9 Claims, 8 Drawing Figures

4,333,128

MIRROR FOR THE APHAKIC EYE

FIELD OF THE INVENTION

This invention relates to apparatus for assisting a person having an aphakic eye (i.e. a patient with an eye which has no crystalline lens) to see his own eye clearly without the aid of any external transparent lens or aperture and thereby to assist in the application of a contact lens to the eye.

BACKGROUND OF THE INVENTION

The surgical removal of the crystalline lens of the eye due to a cataract condition or other defect, leaves the eye without the capacity to function unless some form of substitute lens is provided. Eyeglasses can be made to serve the purpose, but the correction required is so great that the lenses are thick and heavy. In addition, due to the magnitude of the correction, the lens provides very little side vision. Moreover, if only one eye is aphakic, it is extremely difficult, if not impossible, to match the vision of the aphakic eye to that of the normal eye with an external lens. Prosthetic crystalline lenses have been inserted surgically and employed with limited success, but they involve the risks of additional surgery as well as the possibility of rejection, and if only one eye is aphakic, matching the prosthetic lens with the normal lens is a serious problem. As a result, the preferred practice is to employ a contact lens to the transparent epithelium covering the cornea of the eye. Suitable contact lenses are small and light and can readily be interchanged for matching to a normal lens. Peripheral vision is no problem with the contact lens because the lens covers the eye aperture and also follows the eye's movement. Once the patient becomes used to the contact lens, it is highly satisfactory. The main problems of the contact lens for the aphakic eye patient have to do with the application and removal of the contact lens. Contact lenses are small, and hard enough to see even with good vision, but the difficulty is compounded for the aphakic eye patient, especially when both eyes are aphakic. Guiding a finger on which a contact lens is balanced to the correct place on the eye is quite difficult with no visual direction, particularly for the more elderly. Another serious problem is finding a lens which may have slipped off the finger and fallen.

The present invention is directed to the solution of these problems of the aphakic eye patient who wishes to use contact lenses. More particularly, an object is to provide the aphakic eye patient with means by which he can see with his aphakic eye without any external transparent lens. Still more particularly an object is to provide such a means for use by the aphakic eye patient while applying or removing a contact lens.

BRIEF DESCRIPTION OF THE INVENTION

The present invention stems from the discovery that a magnifying mirror of a specific nature can be used by an aphakic eye patient to employ his own aphakic eye to see an image of that same eye at an appropriate distance from the mirror and at an appropriate magnification to serve as a visual aid for the application and removal of a contact lens. The required curvature of the mirror (and hence its magnification) falls within a critical range in which the average radius of the mirror is between 4.5" and 9.5", with 7.95" being preferred. A spherical, near spherical or parabolic mirror may be employed. When the radius is increased, focussing becomes increasingly more difficult and soon becomes impossible. As the radius is decreased, the magnification becomes so great that the image of the finger carrying the lens occupies too much of the field. Moreover, with high magnification, slight movements cause undesireably exaggerated motion of the image. Also as the radius is reduced the patient's eye must be brought so near the mirror in order to focus, that little room remains for manipulation of the contact lens.

It is a feature of the invention that when the aphakic eye patient uses the preferred mirror which will be referred to herein as the "aphakic mirror", and appropriately adjusts the position of the head relative thereto, he can bring the image of his own aphakic eye into focus at the retina of that same aphakic eye. Once this image is in focus, the patient can then place a contact lens on his finger and guide it accurately to the eye. Of course, as the finger intercepts the line of vision, the eye does not see in the intercepted area, but this happens only as the finger approaches closely to the eye.

Once the contact lens is in place, the aphakic eye can see as a normal eye sees and the image is no longer focussed by the aphakic mirror. The patient, however, will usually still want to see whether the contact lens is properly in position. Thus, it is a feature of the present invention that the patient is able, by adjusting the distance of his head (and hence the focal plane of his eye) a few inches, again to bring the eye into perfect focus, this time, with the contact lens in place. This, as it were, double function of the mirror is attainable only with the specific range of curvature substantially as above outlined. On the other hand, in some cases, a patient may prefer to examine his aphakic eye with an ordinary flat mirror or with a mirror of much less magnification than the aphakic mirror herein described, and in order to accommodate same, in one embodiment of the invention, an ordinary flat mirror (or one having a minor degree of magnification) is positioned adjacent to the aphakic mirror so that the patient can conveniently shift his head and use the ordinary mirror for normal uses as well as to check the position of the contact lens.

A further feature of the invention is that the mirrors are mounted in a flat box in which light diffusing bulbs are positioned around the mirrors so as to cast soft light from a multiplicity of directions (preferably from three of the four quadrants) onto the face and eye converging at approximately 7" from the mirror, so that a finger positioned closer to the mirror will not be illuminated. The soft light is important because aphakic eyes are particularly sensitive to glare. In addition, directing the light from various directions eliminates confusing shadows. Shielding the finger from the applied light is important in order to concentrate the illumination of the image on the critical part, i.e. the eye. It is also a feature of the invention that the arrangement is flat and can be suitably placed on a table for use by the patient looking down onto it from above. In this way the contact lens is most conveniently balanced on the finger, and, if it falls, it simply falls onto the mirror.

The aphakic mirror does not permit the patient to see the fallen contact lens with his aphakic eye, but it does permit him to hold his head steady and to guide his hand in the conduct of an effective scanning search. Of course, the aphakic mirror can be used to apply a second contact lens with which a visual search for a fallen contact lens may be made.

These and other features of the invention will best be understood and appreciated with reference to the following detailed description of an illustrative embodiment.

DETAILED DESCRIPTION OF THE INVENTION

Figure 3:
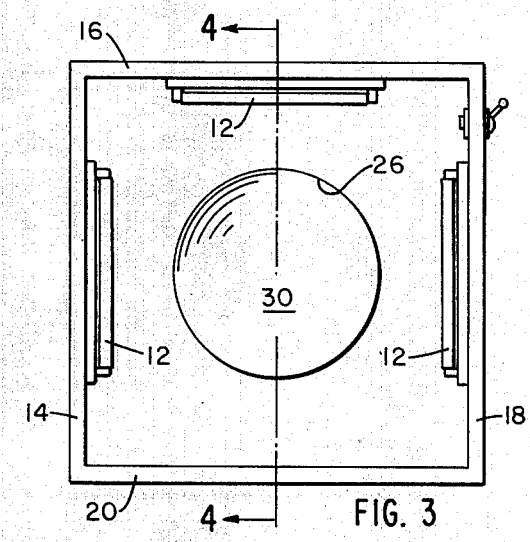
FIG. 3 is a plan view of the device of FIG. 1 with the cover removed to expose the interior.
Figure 5:
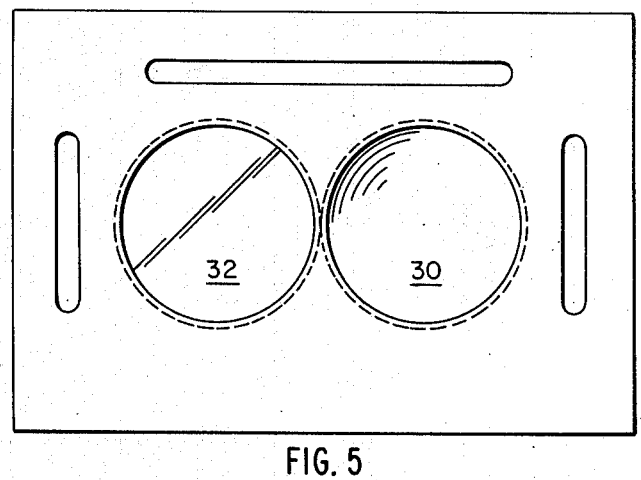
FIG. 5 is a plan view of an embodiment of the invention employing two mirrors, one aphakic and the other conventional side by side.
Figure 4:
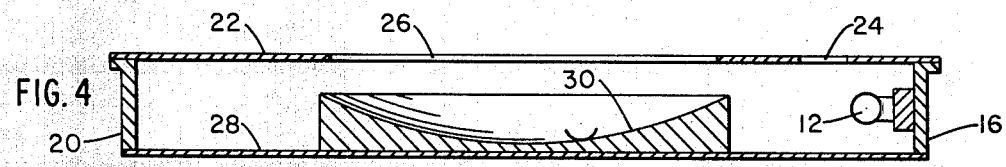
FIG. 4 is a view in cross-section along the lines of 4—4 of FIG. 3.

The illustrative embodiment of the invention herein shown comprises a shallow flat square box 10 about 14" on each side and about 1½" deep. It may conveniently be made of sheet-metal, plywood, or molded plastic. Inside the box (see FIG. 3) are positioned three 6" long fluorescent light bulbs 12 on sides which will be referred to as the left side 14, the away side 16 and the right side 18. The fourth side of box 10 will be referred to as the near side 20.

Box 10 is provided with a cover 22 which is slotted at 24 inwardly of each light bulb with the slots being positioned relative to the bulbs 12 to cause the light emanating from the bulbs 12 to converge over the center of box 10 at a height of about 5½".

Centrally of box 10, cover 22 is provided with a circular aperture 26 of about 6" in diameter. In registration with aperture 26, within box 10 and resting on bottom wall 28 is a circular aphakic mirror 30 of about 7" in diameter.

The aphakic mirror has a concave essentially spherical surface having a radius between about 4.5" and 9.5", and preferably about 7.95".

Figure 1:
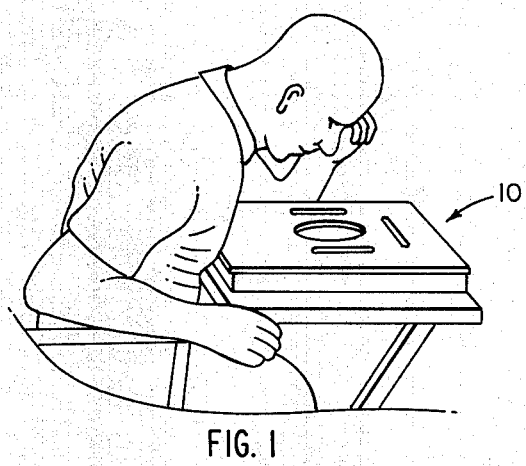
FIG. 1 is a perspective view in side elevation showing an aphakic eye patient using the invention to apply a contact lens.
Figure 2:
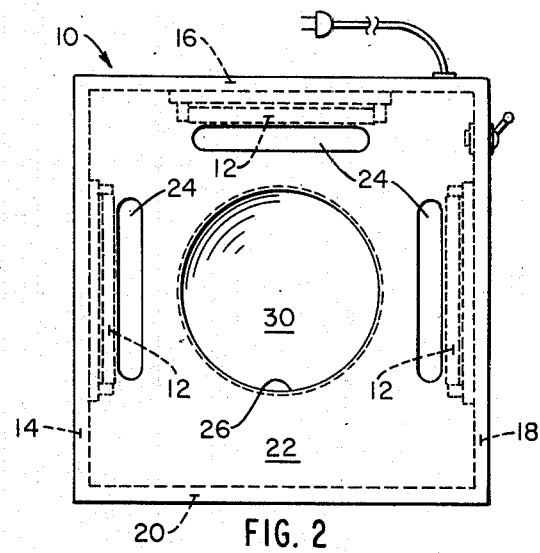
FIG. 2 is a plan view of the device of FIG. 1.

In operation, an aphakic eye patient places box 10 in a level position on a table and leans over from near side 20 as shown in FIG. 1 with the light bulbs 12 illuminated. Diffuse light emanating from bulbs 12 converges on the patient's face primarily in the region of the eyes. Light also passes within the box across the surface of aphakic mirror 30. As the patient peers into mirror 30 and lowers his aphakic eye to about 6" from the mirror, he reaches a point where the reflected real image of his face comes into focus on the retina of his aphakic eye. In this way the patient can suddenly see with his aphakic eye. While this method of vision may well have a substantially broader application, its use, as shown herein, is as an aid to the aphakic eye patient for application and removal of a contact lens. Once the image of the face and eye are in focus, the patient may then place the contact lens on a finger and visually guide the finger toward the aphakic eye. Of course, as the finger makes the final motions which apply the contact lens to the epithelium, the finger itself blocks off the image, but such blockage occurs only at the final moment immediately preceeding contact.

If, by chance, the contact lens happens to fall, since the patient's head is directly above mirror 30, like as not the lens will fall on mirror 30 and be illuminated thereon by the cross light from bulbs 12.

Although a spherical mirror has been described, it is also possible to use one of other symmetrical spheroidal shape including parabolic. In most cases, some distortion of the image occurs at the periphery. Such distortion, however, is not a serious disadvantage. The important point is that the light rays from the object pass via the mirror to form a real image at the retina of the aphakic eye at least in the central area of the image. The user soon learns by bringing his eye toward and away from the mirror, the position at which optimum vision is attained. That some clarity may be lost at the periphery of the image is not critical. Of course, a mirror can be devised with which the clarity will extend substantially further to the sides, but the added expense thereof is not considered worth it for the ordinary user. On the other hand, it is intended that the invention, as claimed herein, cover any of the three ways of doing it and variations therebetween, i.e. by use of a spherical aphakic mirror, a parabolic aphakic mirror, or by an aphakic mirror ground specifically for expansion of the peripheral vision of the aphakic eye. As long as the general, or average radius of the curvature of each mirror is within the critical range of 4.5" to 9.5", it will be usable as an aphakic mirror as an aid to contact lens insertion and removal according to the present invention.

In addition, it is not necessary to employ an expensive optical surface. The mirror can be a glass mirror or it can be made of molded plastic having a polished and aluminized surface. An aluminized front face mirror on polished glass suitable for astronomy would, of course, be better but the specific use herein involved, does not require it.

In one embodiment of the invention a conventional flat (or slightly concave) mirror 32 is employed adjacent to aphakic mirror 30 to provide the patient with a means for checking the position of the contact lens on the eye once it has been applied.

Figure 6:
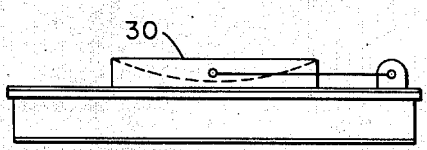
FIGS. 6, 7, and 8 are diagrammatic views in side elevation of an arrangement employing an aphakic mirror and a conventional mirror back-to-back and a pivotal mount whereby the user can flip from one to the other as desired.
Figure 7:
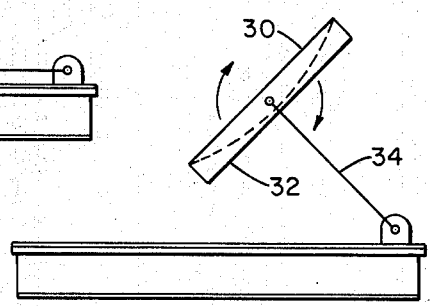
Figure 8:
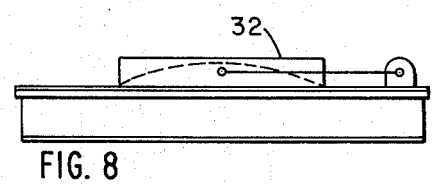

Mirrors 30 and 32 can also be mounted back-to-back in relation as shown in FIGS. 6–8, and hinged to box 10 by pivot arms 34 so that switching from the aphakic mirror 30 to conventional mirror 32 may be done by the patient without having to move his head.

In view of the foregoing, numerous variations and/or adaptations of the invention will now be apparent to those skilled in the art. For example, a crescent shaped fluorescent bulb and appropriately shaped slots may be used. Direct current bulbs may be employed using a rechargeable battery as a source of electricity. Accordingly, it is intended that the invention not be confined to the details herein described but rather that it be limited only by the definitions and terms of the appended claims.

I claim:

1. Apparatus for providing vision to the aphakic eye without the use of either an external aperture or an external transparent lens comprising reflecting means for gathering rays of light from an illuminated portion of the face of a person having an aphakic eye and reflecting same back toward the aphakic eye, said reflecting means positioned a distance from the face of said person appropriate for self examination of the eye and for the insertion, removal, and adjustment of a contact lens, and the curvature of said reflecting means selected in relation to the distance of the image from the reflecting means to cause rays of light emanating from said eye to form, when modified by the combined refraction of the epithelium and cornea and vitreous humor of said eye, an image at the retina of said aphakic eye, whereby said aphakic eye perceives an image of itself.

2. The apparatus defined in claim 1 further characterized by the general radius of said reflecting means being between about 4.5 inches and 9.5 inches, whereby the distance between said eye and said reflecting means is between about 4" and 12" when the image is in focus.

3. The apparatus defined in claim 1 further characterized by said reflecting means being spherical.

4. The apparatus defined in claim 1 further characterized by said reflecting means being parabolic.

5. The apparatus defined in claim 1 further characterized by said reflecting means is symmetrically spheroidal.

6. The apparatus defined in claim 2 further characterized by a conventional mirror adapted for inspection of the aphakic eye by a normal eye or by an aphakic eye equipped with an external lens, said conventional mirror positioned adjacent to the reflecting means.

7. The apparatus defined in claim 2 further characterized by means spaced laterally of said reflecting means for directing diffused light onto said object from a multiplicity of lateral angles permitting illumination of said object without shadows, but without illuminating a hand balancing a contact lens positioned generally over said reflecting means but closer to said reflecting means.

8. The apparatus defined in claim 7 further characterized by additional means for directing light across said reflecting means to illuminate a contact lens resting on said reflecting means.

9. The apparatus defined in claim 2 further characterized by means for pivotally mounting said reflecting and an ordinary mirror connected to said reflecting means in back-to-back relation whereby a user may flip the reflecting means over and use the ordinary mirror to inspect the position of a contact lens on the aphakic eye.

* * * * *